United States Patent [19]

Veber et al.

[11] 4,098,777

[45] Jul. 4, 1978

[54] PROCESS FOR THE PREPARATION OF PYROGLUTAMYL-ALA-LYS-SER-GLN-GLY-GLY-SER-ASN

[75] Inventors: Daniel F. Veber, Ambler; Robert G. Strachan, Warrington, both of Pa.

[73] Assignee: Merck & Co., Inc., Rahway, N.J.

[21] Appl. No.: 777,226

[22] Filed: Mar. 14, 1977

[51] Int. Cl.² .................................................. C07C 103/52
[52] U.S. Cl. ................................................. 260/112.5 R
[58] Field of Search ................................... 260/112.5 R

[56] References Cited

PUBLICATIONS

J. Bach, et al., Nature 266, 55 1977.

Wolters, et al., J. Org. Chem. 39, 1974 pp. 3388–3392.

*Primary Examiner*—Delbert R. Phillips
*Attorney, Agent, or Firm*—Walter Patton

[57] ABSTRACT

This invention is directed to the chemical process for the preparation of the polypeptide, pyroglutamyl-Ala-Lys-Ser-Gln-Gly-Gly-Ser-Asn and to intermediates in said process. The polypeptide prepared by the present process is useful in the treatment of autoimmune diseases such as Lupus like pathology and specifically for the treatment of Lupus Erythematosus in man. This polypeptide is also useful for selectively stimulating T-cell activity in aging subjects.

8 Claims, No Drawings

PROCESS FOR THE PREPARATION OF PYROGLUTAMYL-ALA-LYS-SER-GLN-GLY-GLY-SER-ASN

BACKGROUND OF THE INVENTION

It has been reported that the injection of thymic cell-free extracts can restore the immunological function of neonatally thymectomized mice to reject skin grafts. Data showing partial reconstitution of neonatally thymectomized mice by thymus grafts in a Millipore chamber has suggested that the thymus acts as an endocrine gland and elaborates a hormone into the blood circulation. [See D. Osoba, et al., Nature 199, 359 (1963)]. This medicinally useful hormone has been isolated and is believed to be a polypeptide having the amino acid sequence: <Glu-Ala-Lys-Ser-Gln-Gly-Gly-Ser-Asn. [See Bach et al., Comptes Rendes, 283 No. 14, 1605–1609 (1976)].

In general, the hormone is obtained in small quantities from pig blood by a laborious process involving defibrination, dialysis and concentration on a suitable filter followed by fractionation through a molecular sieve, chromatography on an ion-exchange resin followed by further fractionation by thin layer chromatography and finally by electrophoresis. Each step of the isolation is monitored by a bioassay which is based on the property of the peptide which inhibits the formation of rosettes in the presence of azathioprine.

The novel polypeptide obtained by the above process is useful in the treatment of autoimmune diseases such as lupus like pathology and specifically for the treatment of Lupus Erythematosus in man and for selectively stimulating T-cell activity in aging subjects.

According to the process of the present invention the peptide, <Glu-Ala-Lys-Ser-Gln-Gly-Gly-Ser-Asn, is readily prepared in large quantities by chemical means.

SUMMARY OF THE INVENTION

This invention is concerned with the process for the chemical preparation of the nonapeptide having the structure: pyroglutamyl-Ala-Lys-Ser-Gln-Gly-Gly-Ser-Asn. The process comprises of a combination of solid phase peptide synthesis and stepwise condensation of amino acids carried out in solution. The intermediates produced in the preparation of the nonapeptide represent an additional aspect of the invention.

According to the process of the present invention the nonapeptide, <Glu-Ala-Lys-Ser-Gln-Gly-Gly-Ser-Asn, is prepared by the condensation of two smaller peptide fragments. The preferred process is to condense the carboxylic acid group of the N-terminal heptapeptide, or N-terminal hexapeptide with the corresponding amino group of the C-terminal dipeptide or C-terminal tripeptide. In either process, the carboxylic acid group participating in the condensation is borne by the optically inactive glycyl moiety. The amino acid bearing the carboxylic acid group participating in the condensation is most prone to racemization. Accordingly, the process of the present invention avoids the possibility of racemization.

According to the process of the present invention, the N-terminal heptapeptide or hexapeptide is prepared by the solid phase method and the corresponding C-terminal dipeptide or tripeptide is prepared in solution. The advantage of this process is that the first amino acid attached to the solid phase is glycine which has no optically active center.

The abbreviated designations, which are used herein for the amino acid components, certain preferred protecting groups, amino acid activating groups, condensing agents, reagents and solvents employed in the process of this invention are as follows:

TABLE I

| Abbreviated Designation | Amino Acid |
|---|---|
| <Glu | pyroglutamic acid |
| Ala | L-alanine |
| Lys | L-lysine |
| Ser | L-serine |
| Gln | L-glutamine |
| Gly | glycine |
| Asn | L-asparagine |

| Abbreviated Designation | Protecting Groups |
|---|---|
| INOC | isonicotinyloxycarbonyl |
| BOC | tert-butyloxycarbonyl |
| OMe | methyl ester |
| tBu | tert-butyl |
| CBZ | benzyloxycarbonyl |
| Bzl | benzyl |
| 2-Cl-CBZ | 2-chlorobenzyloxycarbonyl |
| TROC | trichloroethoxycarbonyl |
| FMOC | 9-fluorenylmethoxycarbonyl |

| Abbreviated Designation | Activating Groups |
|---|---|
| ONp | p-nitrophenyl ester |
| HSE | N-hydroxysuccinimide ester |
| HBT | 1-hydroxybenzotriazole |

| Abbreviated Designation | Condensing Agents |
|---|---|
| DCCI | dicyclohexylcarbodiimide |

| Abbreviated Designation | Reagents |
|---|---|
| TFA | trifluoroacetic acid |
| TEA | triethylamine |
| DIPEA | diisopropylethylamine |
| IAN | isoamyl nitrite |

| Abbreviated Designation | Solvents |
|---|---|
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

DESCRIPTION OF THE PREFERRED EMBODIMENTS

In accordance with the process of the present invention, the nonapeptide, pyroglutamyl-Ala-Lys-Ser-Gln-Gly-Gly-Ser-Asn, is prepared by condensing the suitably blocked heptapeptide, <Glu-Ala-Lys-Ser-Gln-Gly-Gly with the suitably hydroxy blocked or unblocked dipeptide Ser-Asn and removing the protecting groups. The blocked heptapeptide is prepared by solid phase synthesis and the blocked or unblocked dipeptide is prepared in solution.

Alternately, the nonapeptide, pyroglutamyl-Ala-Lys-Ser-Gln-Gly-Gly-Ser-Asn, is prepared by condensing the suitably blocked hexapeptide, pyroglutamyl-Ala-Lys-Ser-Gln-Gly, with the suitably hydroxy blocked or unblocked tripeptide Gly-Ser-Asn. The hexapeptide is prepared by the solid phase method and the tripeptide by the solution method.

According to the process of the present invention, the synthesis of the blocked heptapeptide by the solid phase technique is conducted in a stepwise manner on chloromethylated resin. The resin in composed of fine beads (20–70 microns in diameter) of a synthetic resin prepared by copolymerization of styrene with 1 to 2 percent divinylbenzene. The benzene rings of the resin are chloromethylated in a Friedel-Crafts reaction with chloromethyl methyl ether and stannic chloride. The Friedel-Crafts reaction is continued until the resin contains 0.5 to 5 mmole of chlorine per gram of resin. The chlorine in benzyl chloride is reactive and undergoes reaction with carboxylic acid groups in the presence of base to form the corresponding benzyl ester.

Glycine, the C-terminal amino acid of the heptapeptide, is converted to its amino protected derivative. The carboxyl group of glycine is bound covalently to the insoluble polymeric resin support as the corresponding carboxylic acid benzyl ester. After the amino protecting group of glycine is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, 1-hydroxybenzotriazole ester and the like. Deprotection and addition of successive amino acids is performed until the desired heptapeptide is formed. The C-terminal hexapeptide can be prepared in a similar manner.

It is to be understood that, in the process of the present invention <Glu-Ala-($\epsilon$-R)Lys-(O-$R_1$)Ser-Gln-Gly-Gly-O-$CH_2$-$\phi$-resin can also be prepared by reacting Ala-($\epsilon$-R)Lys-(O-$R_1$)Ser-Gln-Gly-Gly-O-$CH_2$-$\phi$-resin with BOC-Gln and removing the BOC-group with TFA. The resulting N-terminal glutaminyl moiety spontaneously cyclizes to <Glu.

After the heptapeptide has been formed on the solid phase resin, it may be removed by a variety of methods. For example, the peptide may be cleaved from the resin with hydrazine and thus directly form the peptide hydrazide which may be subsequently converted to the azide and condensed with the suitably hydroxy blocked or unblocked dipeptide Ser-Asn. Alternatively, the peptide may be removed from the resin by treatment with a lower alcohol such as methanol in the presence of an organic base such as triethylamine, thus resulting in the formation of the corresponding lower alcohol ester of the heptapeptide. The esters are converted to the azide via the hydrazide which azide may be reacted with the suitably hydroxy blocked or unblocked dipeptide Ser-Asn to obtain the desired blocked nonapeptide.

The hydrazide is converted to the corresponding azide by reaction with a reagent which furnishes nitrous acid in situ. Suitable reagents for this purpose include a lower alkyl nitrite (e.g., t-butyl nitrite, isoamyl nitrite) or an alkali metal nitrite salt (e.g., sodium nitrite, potassium nitrite) in the presence of a strong acid such as hydrochloric, phosphoric, sulfonic, etc. This reaction is carried out in the presence of either water and/or a non-aqueous solvent such as dimethylformamide, tetrahydrofuran, dioxane, chloroform, methylene chloride, etc., at a temperature between about $-40°$ C. and $+20°$ C. The azide which is preferably not isolated from the reaction medium is then coupled with a suitably hydroxy blocked or unblocked dipeptide Ser-Asn to obtain the desired blocked nonapeptide. This coupling is carried out between a temperature of about $-50°$ C. and $+50°$ C., preferably between about $-35°$ C. and $+10°$ C.

The selection of the protecting group for the $\epsilon$-amino of lysyl is, in part, dictated by the reagents employed in cleaving the blocked hepta- or hexapeptide from the resin.

Table III indicates a process for cleaving a blocked heptapeptide from the resin with MeOH/TEA. Accordingly, the $\epsilon$-amino protecting groups are selected from those which are stable to treatment with MeOH/TEA and to the subsequent treatment with $NH_2$—$NH_2$. Under these reaction conditions the formyl, tosyl and variously substituted oxycarbonyls may be used to protect the lysyl $\epsilon$-amino. Suitable $\epsilon$-amino protecting groups are defined by the term R under Table III.

Table IV indicates a process for cleaving a blocked heptapeptide from the resin by treatment with HF or anhydrous HBr in a suitable solvent. Under these reaction conditions trifluoroacetyl and phthaloyl in addition to variously substituted oxycarbonyl groups may be used to protect the lysyl $\epsilon$-amino group. The values of $R_3$, recited under Table IV, represent suitable lysyl $\epsilon$-amino protecting groups useful under these conditions.

The preferred blocking group for the lysyl $\epsilon$-amino group is INOC.

In Table III, $R_1$ and $R_2$ represent the hydroxy protecting groups of the seryl moieties. $R_1$ and $R_2$ are independently selected from the group consisting of benzoyl, t-butyl and benzyl. The benzoyl group is labile to treatment with base, such as $NH_2$—$NH_2$ and hydroxide ion. After the treatment of the blocked heptapeptide methyl ester with $NH_2$—$NH_2$ the benzoyl group is cleaved. Accordingly, $R_1'$ has only the values hydrogen, t-butyl and benzyl. After completion of the synthesis of the blocked nonapeptide, the t-butyl and benzyl groups can be removed with HF or the benzyl group can be selectively removed by treatment with $H_2$, Pd/C.

Reference to Table IV indicates that cleaving the resin bound blocked heptapeptide with anhydrous HF or HBr results in the simultaneous removal of all the seryl hydroxy protecting groups, $R_4$, with the exception of p-nitrobenzyl and benzoyl groups. The p-nitrobenzyl group is removed by $H_2$, Pd/C during the last step of the synthesis. Removal of benzoyl requires treatment with a base, such as $NH_2$—$NH_2$.

The suitably blocked dipeptide, Ser-Asn, is prepared in solution by conventional means. For example, Asn is condensed with an amino protected and hydroxy protected or unprotected Ser active ester. The amino protecting group is removed to obtain the suitably hydroxy blocked or free dipeptide Ser-Asn. Alternately, both the amino and hydroxy protecting groups may be removed.

The seryl moiety in the dipeptide, Ser-Asn of Tables III and IV and in the tripeptide, Gly-Ser-Asn of Table VI may optionally remain unblocked.

N-Terminal amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the $\alpha$-amino group in the amino acids undergoing reaction at the carboxyl end of said amino acid. The BOC protecting group is readily removed following such coupling reaction and prior to the subsequent step by the relatively mild action of acids (i.e., trifluoro acetic acid, or anhydrous hydrogen chloride in ethyl acetate).

The reagents required for carrying out the final deblocking step in Table III and IV depend on which protective groups, R, $R_1'$, $R_2$, $R_3$, $R_4'$ and $R_5$ are present. Table II indicates the reagent or reagents necessary for removing said protective groups. Depending on which combinations of protective groups and deblocking steps are employed, more than one reagent may be necessary for their complete removal. For example treatment of a blocked nonapeptide containing an ε-INOC group and an O-Bzl group with HF-anisole results in the removal of only the O-Bzl group. A second deblocking step using H₂, Pd/C is necessary to remove the ε-INOC group. Alternately, initial treatment with H₂, Pd/C removes both groups.

wherein
R is the protecting group for the ε-amino of the lysyl moiety selected from the group consisting of formyl, toluene sulfonyl, benzyloxycarbonyl; 2,6-dichlorobenzyloxycarbonyl, p-nitrobenzyloxycarbonyl, 2-bromobenzyloxycarbonyl, 2-chlorobenzyloxycarbonyl; 2,2,2-trichloroethoxycarbonyl and isonicotinyloxycarbonyl;
$R_1'$ is hydrogen, t-butyl or benzyl;

TABLE II

| R | HF-anisole | Na/NH₃ | H₂,Pd/C | HBr/HOAc | HCl | Dil. aq. HCl or alc.-HCl | NH₂NH₂ | Oil. Base | Zn-H+ |
|---|---|---|---|---|---|---|---|---|---|
| formyl | — | — | — | — | — | D | — | — | — |
| toluene sulfonyl | — | D | — | — | — | — | — | — | — |
| benzyloxycarbonyl | D | D | D | D | — | — | — | — | — |
| 2-chloro- and 2,6-dichlorobenzyloxy-carbonyl | D | D | D | — | — | — | — | — | — |
| p-nitrobenzyloxycarbonyl | — | D | D | — | — | — | — | — | D |
| 2-bromobenzyloxycarbonyl | D | D | D | — | — | — | — | — | — |
| 2,2,2-trichloroethoxycarbonyl | — | — | — | — | — | — | — | — | D |
| isonicotinyloxycarbonyl | — | D | D | — | — | — | — | —D | — |
| $R_1R_2'$, $R_2$, $R_4$, $R_4'$ and $R_5$ | | | | | | | | | |
| benzyl, o-chlorobenzyl and p-nitrobenzyl t-butyl | D | D | D | D | — | — | — | — | — |
| benzoyl | D | — | — | D | D | — | — | — | — |
|  | — | D | — | — | — | — | D | D | — |
| $R_3$ | | | | | | | | | |
| isonicotinyloxycarbonyl | — | D | D | — | — | — | — | — | D |
| trifluoroacetyl | — | D | — | — | — | D | D | D | — |
| phthaloyl | — | * | — | — | — | D | D | — | — |
| toluene sulfonyl | — | D | — | — | — | — | — | — | — |
| p-nitrobenzyloxycarbonyl | — | D | D | — | — | — | — | — | D |
| 2,2,2-trichloroethoxycarbonyl | — | — | — | — | — | — | — | — | D |
| 9-fluoroenylmethoxycarbonyl | — | D | — | — | — | — | D | D | — |

D = deblocked
* = destroyed $R_2$ is hydrogen or
$R_1$ and $R_2$ are protecting groups for the hydroxy group of the seryl moieties, independently selected from the group consisting of benzoyl, t-butyl and benzyl.

TABLE III
Scheme for Preparing <Glu-Ala-Lys-Ser-Gln-Gly-Gly-Ser-Asn

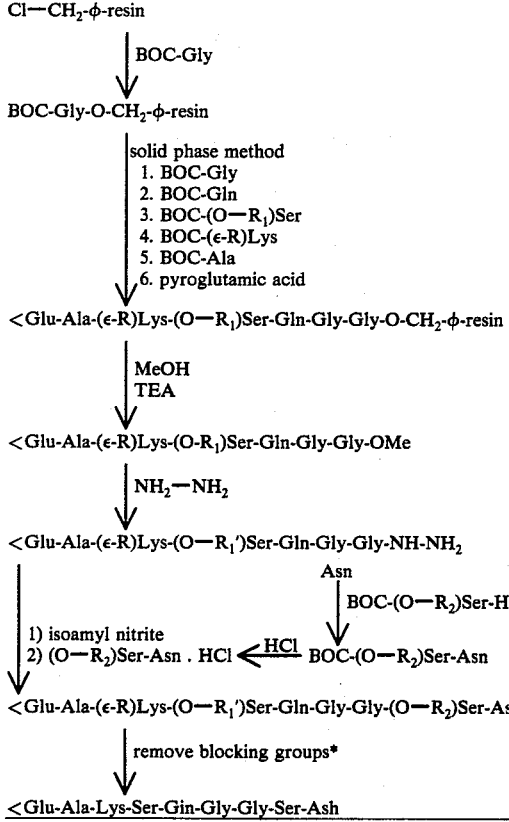

*Reagents appropriate for removal of R, $R_1'$ and $R_2$ are set forth in Table II.

TABLE IV
Scheme for Preparing <Glu-Ala-Lys-Ser-Gln-Gly-Gly-Ser-Asn

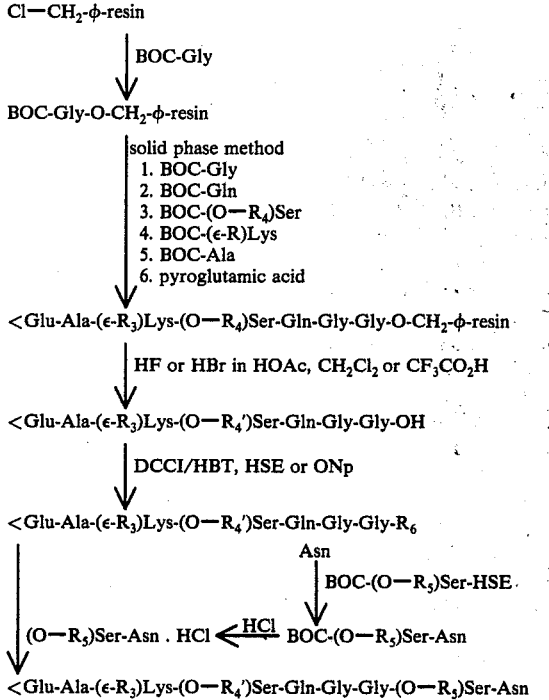

TABLE IV-continued
Scheme for Preparing <Glu-Ala-Lys-Ser-Gln-Gly-Gly-Ser-Asn

|  remove protecting groups*

<Glu-Ala-Lys-Ser-Gin-Gly-Gly-Ser-Ash

*Reagents appropriate for removal of $R_3$, $R_4'$ and $R_5$ are set forth in Table II.

wherein
$R_3$ is the protecting group for the ε-amino of the lysyl moiety selected from the group consisting of INOC, trifluoroacetyl, phthaloyl, tosyl, p-nitrobenzyloxycarbonyl, TROC and FMOC; in the case wherein $R_3$ is FMOC, treatment with base is necessary for its removal;

$R_4$ and $R_5$ are independently hydrogen or protecting groups for the hydroxy group of the seryl moieties, independently selected from the group consisting of benzyl, substituted benzyl wherein the substituent is o-chloro or p-nitro; t-butyl and benzoyl;

$R_4'$ is hydrogen, p-nitrobenzyl or benzoyl;

$R_6$ is an active ester selected from the group consisting of 1-hyroxybenzotriazole, N-hydroxysuccinimide and p-nitrophenyl.

TABLE V
Scheme for Preparing <Glu-Ala-Lys-Ser-Gin-Gly-Gly-Ser-Ash

Cl—CH$_2$-φ-resin

|  BOC-Gly

BOC-Gly-O-CH$_2$-φ-resin

TABLE V-continued
Scheme for Preparing <Glu-Ala-Lys-Ser-Gin-Gly-Gly-Ser-Ash solid phase method
1. BOC-Gly
2. BOC-Gln
3. BOC-(O-Bzl)Ser
4. BOC-(ε-INOC)Lys
5. BOC-Ala
6. pyroglutamic acid <Glu-Ala-(ε-INOC)Lys-(O-Bzl)Ser-Gln-Gly-Gly-O-CH$_2$-φ-resin

|  MeOH
|  TEA

<Glu-Ala-(ε-INOC)Lys-(O-Bzl)Ser-Gln-Gly-Gly-OMe

|  NH$_2$—NH$_2$

<Glu-Ala-(ε-INOC)Lys-(O-Bzl)Ser-Gln-Gly-Gly-NH-NH$_2$

Asn
|  BOC-(O-Bzl)Ser-HSE 1) isoamyl nitrite
2) (O-Bzl)Ser-Asn . HCl ←HCl— BOC-(O-Bzl)Ser-Asn <Glu-Ala-(ε-INOC)Lys-(O-Bzl)Ser-Gln-Gly-Gly-(O-Bzl)Ser-Asn

|  HF-anisole

<Glu-Ala-(ε-INOC)Lys-Ser-Gln-Gly-Gly-Ser-Asn

|  H$_2$, Pd/C

<Glu-Ala-Lys-Ser-Gln-Gly-Gly-Ser-Ash

TABLE VI
Scheme for Preparing <Glu-Ala-Lys-Ser-Gln-Gly-Gly-Ser-Asn

Cl—CH$_2$-φ-resin

|  BOC-Gly

BOC-Gly-O-CH$_2$-φ-resin solid phase method
1. BOC-Gln
2. BOC-(O-Bzl)Ser
3. BOC-(ε-INOC)Lys
4. BOC-Ala
5. pyroglutamic acid <Glu-Ala-(ε-INOC)Lys-(O-Bzl)Ser-Gln-Gly-O-CH$_2$-φresin Asn
|T
|  N-BOC-(O-Bzl)Ser-HSE

|  MeOH
|  TEA

N-BOC-(O-Bzl)Ser-Asn

<Glu-Ala-(ε-INOC)Lys-(O-Bzl)Ser-Gln-Gly-OMe

|  HCl

|  NH$_2$—NH$_2$

<Glu-Ala-(ε-INOC)Lys-(O-Bzl)Ser-Gln-Gly-NH-NH$_2$ (O-Bzl)Ser-Asn

|  BOC-Gly-HSE 1) isoamyl nitrite
2) Gly-(O-Bzl)Ser-Asn . HCl   ←—HCl—BOC-Gly-(O-Bzl)Ser-Asn <Glu-Ala-(ε-INOC)Lys-(O-Bzl)Ser-Gln-Gly-Gly-(O-Bzl)Ser-Asn

|  HF-anisole

<Glu-Ala-(ε-INCO)Lys-Ser-Gln-Gly-Gly-Ser-Asn

| TABLE VI-continued |
| --- |
| Scheme for Preparing <Glu-Ala-Lys-Ser-Gln-Gly-Gly-Ser-Asn |

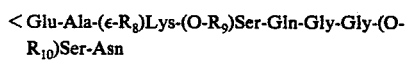

As reference to Table V shows, the preferred overall procedure for preparing the desired nonapeptide, pyroglutamyl-Ala-Lys-Ser-Gln-Gly-Gly-Ser-Asn, involves the stepwise synthesis of the blocked heptapeptide, <Glu-Ala-(ε-INOC)Lys-(O-Bzl)Ser-Gln-Gly-Gly-O-CH$_2$-φ-resin, on a solid phase resin. More specifically, the carboxyl end of BOC-Gly is bound covalently to an insoluble polymeric resin support as the carboxylic acid benzyl ester. After the attachment of the BOC-Gly is completed on the resin, the BOC protecting group is removed by treatment with TFA in CH$_2$Cl$_2$. The subsequent amino acids are attached, in the form of BOC-amino acids, using DCCI as the condensing agent. In the case of the condensation of BOC-Gln and <Glu, 1-hydroxybenzotriazole is added to the reaction mixture in addition to DCCI. Each coupling step may be performed twice in order to insure complete reaction.

After the desired blocked heptapeptide has been formed, it is removed from the resin by treatment with methanol in the presence of triethylamine (TEA). The resulting blocked heptapeptide having the amino acid sequence: <Glu-Ala-(ε-INOC)Lys-(O-Bzl)Ser-Gln-Gly-Gly-OMe is treated with hydrazine to form the corresponding hydrazide. The resulting hydrazide is treated with isoamyl nitrite in acid pH to form the corresponding azide. The blocked heptapeptide azide is treated with the dipeptide, (O-Bzl)Ser-Asn.HCl, to form the blocked nonapeptide, <Glu-Ala(ε-INOC)Lys-(O-Bzl)Ser-Gln-Gly-Gly-(O-Bzl)Ser-Asn. The O-Bzl groups are removed by treatment with HF in the presence of anisole and the ε-INOC group is removed by hydrogenation in the presence of Pd/C to give the desired peptide, pyroglutamyl-Ala-Lys-Ser-Gln-Gly-Gly-Ser-Asn.

The dipeptide, (O-Bzl)Ser-Asn.HCl, is prepared by condensing Asn with the blocked amino acid active ester, BOC-(O-Bzl)Ser-HSE, to form the blocked dipeptide, BOC-(O-Bzl)Ser-Asn. The N-terminal protecting group, BOC, is selectively removed by treatment with anhydrous HCl.

The nonapeptide obtained by the process of Table V is purified by chromatography, preferably on silica gel eluted with chloroform-methanol-water containing 1% acetic acid.

Included in the present invention are the intermediate compounds having the structure,

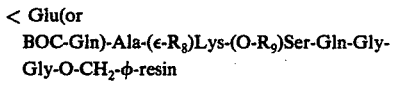

wherein
R$_8$ is the protecting group for the ε-amino of the lysyl moiety selected from the group consisting of formyl, toluene sulfonyl, benzyloxycarbonyl; 2,6-dichlorobenzyloxycarbonyl, p-nitrobenzyloxycarbonyl, 2-bromobenzyloxycarbonyl, 2-chlorobenzyloxycarbonyl; 2,2,2-trichloroethoxycarbonyl, isonicotinyloxycarbonyl, trifluoroacetyl, phthaloyl, TROC and FMOC;

R$_9$ and R$_{10}$ are independently hydrogen or
R$_9$ and R$_{10}$ are protecting groups for the hydroxy group of the seryl moieties, independently selected from the group consisting of benzoyl, t-butyl, benzyl and substituted benzyl wherein the substituent is o-chloro or p-nitro and the compounds having the structure,

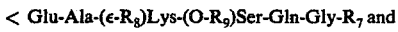

wherein
R$_8$ is as defined above,
R$_9$ is hydrogen or the protecting group for the hydroxy group of the seryl moiety, selected from the group consisting of benzoyl, t-butyl, benzyl and substituted benzyl wherein the substituent is o-chloro or p-nitro,
R$_7$ is —NH—NH$_2$, OH, 1-oxybenzotriazole, N-oxysuccinimide, p-nitrophenoxy or OCH$_3$.

Included in the present invention are the resin bonded intermediates having the structure:

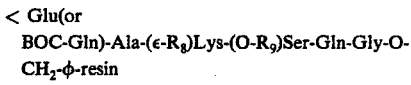

wherein R$_8$ and R$_9$ are as defined above.

Further intermediates contemplated by the present invention are the blocked hexapeptides and blocked resin bound hexapeptides having the structure:

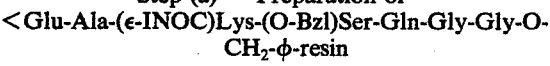

wherein R$_8$, R$_9$ and R$_7$ are as defined above.

The following examples illustrate methods of carrying out the present invention, but it is to be understood that these examples are given for purposes of illustration and not of limitation.

EXAMPLE 1

Preparation of
<Glu-Ala-Lys-Ser-Gln-Gly-Gly-Ser-Asn

Step (a) — Preparation of
<Glu-Ala-(ε-INOC)Lys-(O-Bzl)Ser-Gln-Gly-Gly-O-CH$_2$-φ-resin Chloromethyl resin (2% cross-linked Merrifield resin), 1000 g. (2.75 moles), having 2.75 meq. chlorine/g., and 481.8 g. (2.75 moles, 1 equivalent) of BOC-Gly were added to 5000 ml. of peroxide-free tetrahydrofuran. The mixture was stirred in an oil bath at 80° C. bath temperature for 45 minutes. Triethylamine, 360 ml., was added and the reaction mixture stirred at 80° C. bath temperature for 66 hours, cooled to 25° C. and transferred to a stirred solid phase reaction column with 3000 ml. of tetrahydrofuran. After removal of the solvent, the resin was washed using the stirred column with:

3 × 2000 ml. of tetrahydrofuran
4 × 6000 ml. of ethanol
1 × 6000 ml. of acetic acid
3 × 6000 ml. of water
3 × 6000 ml. of methanol
3 × 6000 ml. of chloroform.

The BOC-Gly-O-CH$_2$-φ-resin was dried in vacuo at 25° C. to constant weight giving 1255 g. of BOC-Gly-O-CH$_2$-φ-resin containing 0.937 mmole of glycine/g. of resin.

BOC-Gly-O-CH$_2$-φ-resin (2.63 g.; 2.0 mmole) was carried through the procedures in Table VII and VIII using 2 deblockings (2 minutes and 25 minutes) with 25% TFA in methylene chloride, and 2.5 equivalents of BOC-amino acid in the required sequence until the desired blocked heptapeptide-O-CH$_2$-φ-resin was obtained.

DCCI was used as the coupling agent in every step except the coupling of BOC-Gln to Gly-Gly-O-CH$_2$-φ-resin and the coupling of < Glu to Ala-(ε-INOC)Lys-(O-Bzl)-Ser-Gln-Gly-Gly-O-CH$_2$-φ-resin in which case the coupling was carried out in the presence of DCCI and 1-hydroxybenzotriazole monohydrate (HBT.H$_2$O).

The coupling of each amino acid proceeded smoothly. Best yields were obtained when the coupling was repeated in each step. When the coupling was repeated, the initial two chloroform washes, the deblocking step and the succeeding three chloroform washes were all omitted and replaced by a single chloroform wash.

The coupling reactions were carried out in methylene chloride, freshly degassed DMF or a mixture of these two solvents. The N-terminal amino group was blocked with a BOC group in each case; the hydroxy group of Ser was blocked with Bzl and the ε-amino group of Lys with INOC.

The sequence of coupling steps and the solvents used is set forth in Table VIII.

TABLE VII

| Solvent or reagent (number of washes | CHCl$_3$ (2) | 25% TFA in CH$_2$Cl$_2$ (2) | CHCl$_3$ (3) | NEt$_3$- CH$_2$Cl$_2$ (1:9) (2) | CHCl$_3$ (3) CH$_2$Cl$_2$ (3) | BOC AA in CH$_2$Cl$_2$, DMF or a mixture of both | 0.5M DCCI in CH$_2$Cl$_2$ | DMF (1) MeOH (1) DMF (1) MEOH (1) CHCl$_3$ (2) |
|---|---|---|---|---|---|---|---|---|
| Volume ml. | 40 | 40 | 40 | 40 | 40 | 25 ml. | 10 | 40 |
| Time/min. | 5 | 2 and 25 | 2 | 5 and 5 | 2 | 5 | 5 min. coupling 30 min. | 2 |

TABLE VIII

| Protected Amino Acid | Solvent ml. |
|---|---|
| BOC-Gly (0.88 g.) recouple | CH$_2$Cl$_2$, 25 ml. |
| BOC-Gln (1.23 g.) + HBT · H$_2$O (1.53 g.) recouple | DMF, 25 ml. |
| BOC-(O-Bzl)Ser (1.48 g.) recouple | CH$_2$Cl$_2$, 25 ml. |
| BOC-(ε-INOC)Lys (1.91 g.) recouple | DMF, 11 ml. and CH$_2$Cl$_2$, 14 ml. |
| BOC-Ala (0.95 g.) recouple | CH$_2$Cl$_2$, 25 ml. |
| <Glu (0.65 g.) + HBT · H$_2$O (1.53 g.) recouple | DMF, 25 ml. |

After the sequence of Table VII and VIII were completed, the blocked heptapeptide-O-CH$_2$-φ-resin was filtered, washed with MeOH 3 × 40 ml. (3 minutes per wash) and dried overnight in vacuo. It weighed 4.67 grams.

Step (b) — Preparation of < Glu-Ala-(ε-INOC)Lys-(O-Bzl)Ser-Gln-Gly-Gly-OMe

The blocked heptapeptide-resin (4.67 g.), prepared by the process set forth in Example 1, Step (a), was suspended in 187 ml. MeOH to which was added 33 ml. TEA. The suspension was stirred for 51½ hours at which time a considerable amount of white solid was present in the mixture. To this mixture was added 50 ml. DMF and 50 ml. 50% HOAc to dissolve everything in the mixture except the resin. The resin was removed by filtration and washed with 50% HOAc. The combined washings and filtrate were concentrated in vacuo to near dryness. The residual moist solid was slurried with 25 ml. ethyl acetate and collected by filtration. The filtered solid was washed with ethyl acetate 2 × 10 ml. and dried in vacuo overnight to yield 1.57 g. of product. TLC in chloroform:methanol:water (80:20:1) on silica gel plates indicated a major spot at R$_f$ 0.5.

Step (c) — Preparation of < Glu-Ala-(ε-INOC)Lys-(O-Bzl)Ser-Gln-Gly-Gly-NH-NH$_2$ The blocked heptapeptide-OMe (1.57 g., 1.75 mmole), prepared by the process set forth in Example 1, Step (b), was slurried in 4 ml. MeOH containing 2 ml. hydrazine. The mixture was stirred at room temperature for 15 minutes and concentrated in vacuo to dryness. The resulting residue was twice resuspended in methanol and concentrated in vacuo to dryness. The residue was triturated with methanol and the resulting solid collected by filtration, washed with methanol and dried to yield 0.5547 g. of product. The washings and filtrates were combined and concentrated to dryness in vacuo. The residue was triturated with ether and the resulting solid collected by filtration, washed with ether and dried to give an additional 0.437 g. of product. TLC in chloroform:methanol:water (50:40:10) indicated a major spot at R$_f$ 0.72. The two fractions were combined to give 0.991 g. of blocked heptapeptide-NH-NH$_2$.

Step (d) — Preparation of < Glu-Ala-(ε-INOC)Lys-(O-Bzl)Ser-Gln-Gly-Gly-O-Bzl-Ser-Asn The blocked heptapeptide-NH-NH$_2$ (0.9914 g., 1.105 mmole), prepared by the process set forth in Example 1, Step c), was slurried in 10 ml. freshly degassed DMF under a nitrogen atmosphere. The reaction mixture was cooled to −25° C. in a MeOH/H$_2$O (50:50) - dry ice bath. To this suspension was added 1.05 ml. of 5.24N HCl in THF (5.52 meq. HCl). To the resulting clear acidic solution of "pH" 1 was added 148 mg. isoamyl nitrite (1.26 mmole) over a period of 2½ hours and stirring continued for 1 hour. This solution of < Glu-Ala- (ε-INOC)Lys-(O-Bzl)Ser-Gln-Gly-Gly-N₃ was cooled to −35° C. and treated with a 1 ml. DMF solution containing 382 mg. (1.215 mmole, 10% excess) of (O-Bzl)Ser-Asn.HCl, prepared by the process set forth in Example 2. The solution was maintained under a nitrogen atmosphere and allowed to warm to −20° C. during which time the "pH" was maintained at 7.6 to 7.8 by the addition of N,N-diisopropylethylamine (DIPEA). The solution was maintained at −20° C. for 24 hours, the "pH" adjusted to 7.6 to 7.8 with DIPEA and then kept at −20° C. for an additional 48 hours.

The solution was concentrated in vacuo and the residue triturated with MeOH to give a solid. The solid was collected by filtration and dried in vacuo overnight to give 1.3 g. of crude blocked nonapeptide.

Step (e) — Preparation of < Glu-Ala-(ε-INOC)Lys-Ser-Gln-Gly-Gly-Ser-Asn

The blocked nonapeptide, (400.0 mg.), prepared by the process set forth in Example 1, Step d), was dissolved in 1 ml. anisole and 10 ml. hydrogen fluoride at −70° C. The solution was stirred magnetically at 0° C. for 1 hour. The excess hydrogen fluoride was removed in vacuo at 0° C. The resulting residue was triturated with 35 ml. ethyl acetate to give a solid. The solid was collected by filtration, washed with ethyl acetate and dried in vacuo to give 252 mg. of crude product.

The above process was repeated on 900 mg. blocked nonapeptide using 2 ml. anisole and 20 ml. hydrogen fluoride. An identical work up yielded 722 mg. of product. The material obtained in the two preparations was combined to yield a total of 974 mg.

The crude (ε-INOC)-nonapeptide (680 mg.) was suspended in a solution of 6.5 ml. H₂O, 30 ml. MeOH and 40 ml. CHCl₃. The insoluble portion (56 mg.) was removed by centrifugation. The supernatant was applied on a column packed with 171 g. silica gel in CHCl₃—MeOH—H₂O (50:40:10) and eluted with the same solvent system. Fractions of 5 ml. were collected. The product appeared in fractions 42 to 80. These fractions were combined and concentrated in vacuo and the residue freeze dried to yield 224 mg. of pure product.

Step (f) — Preparation of <Glu-Ala-Lys-Ser-Gln-Gly-Gly-Ser-Asn

The (ε-INOC)-nonapeptide (220 mg.), prepared by the process set forth in Example 1, Step (e), was dissolved in 10 ml. 5% HOAc in H₂O. To this solution was added 200 mg. 10% Pd/C and the reaction vessel purged with N₂. Hydrogen gas was bubbled through the reaction mixture with ice-bath cooling for a period of 30 minutes. An additional 20 ml. of 5% HOAc in H₂O was added to wash the material down from the sides of the reaction vessel. The reaction mixture was filtered to remove the catalyst. The filtered catalyst was washed with 50 ml. 5% HOAc in H₂O. The filtrates and washings were concentrated to a small volume and the residue freeze dried to give 188 mg. of crude product (100% yield).

Deblocked nonapeptide (100 mg.) was dissolved in 2 ml. of the solvent system CHCl₃—MeOH—H₂O—HOAc (40:47:13:1) with sufficient water and methanol added to complete the solution. The solution was applied on a column packed with 5.0 g. silica gel in the solvent system CHCl₃—MeOH—H₂O—HOAc (40:47:13:1) and the column was eluted with the same solvent system. Fractions of 1 ml. each were collected. The product was found in fractions 40 to 90. These fractions were combined and concentrated in vacuo to obtain 43 mg. of deblocked nonapeptide. A 20 hour acid hydrolysate showed the following amino acid analysis:

|  | μmole/mg. | normalized to glycine |
|---|---|---|
| Lys | 1.05 | 1.01 |
| Asp | 1.07 | 1.03 |
| Ser | 1.97 | 1.90 |
| Glu | 2.14 | 2.06 |
| Gly | 2.07 | 2.00 |
| Ala | 1.06 | 1.02 |

The results indicated the presence of 89% peptide. Optical rotation indicated $[\alpha]_D^{25} = -52.8°$ (C ¼, 5% HOAc) [corrected for 89% peptide content $[\alpha]_D^{25} = -59.3°$ (C ¼, 5% HOAc)].

EXAMPLE 2

Preparation of (O-Bzl)Ser-Asn

Step (a) — Preparation of BOC-(O-Bzl)Ser-Asn

To a solution of 12 ml. water and 3 ml. DMF containing 600 mg. (4 mmole) L-asparagine and 672 mg. (8 mmole) NaHCO₃ was added 1.88 g. (4.8 mmole) BOC-(O-Bzl)Ser-HSE dissolved in 5 ml. DMF. The reaction mixture was stirred at room temperature for 5 hours and concentrated in vacuo to an oil (bath temperature maintained at less than 25° C.). The oil was dissolved in water and acidified with dilute HCl to a pH of 2.5. The product precipitated as an oil. The aqueous supernatent was decanted and the product extracted into ethyl acetate. The combined ethyl acetate layers were washed with water and dried with anhydrous Na₂SO₄ overnight. The ethyl acetate solution was concentrated in vacuo and the residue maintained in vacuo until constant weight. Weight of crude product 1.68 g.

The crude product was dissolved in a minimum volume of CHCl₃—MeOH—H₂O (70:30:3) and applied on a column packed with 260 g. of silica gel in the same solvent mixture. The column was eluted with the same solvent mixture and 10 ml. fractions were collected. Fractions 135 to 200 were combined and concentrated in vacuo to dryness to yield 1.26 g. of product.

Step (b) — Preparation of (O-Bzl)Ser-Asn.HCl

The blocked dipeptide (1.0 g.), prepared by the process set forth in Example 1, Step a), was slurried in 10 ml. of ethyl acetate and cooled to 0° C. A stream of anhydrous HCl gas was bubbled into the reaction mixture vigorously for a period of 10 minutes at which time complete solution resulted. The reaction vessel was purged with N₂ at 0° C. for 45 minutes and the product appeared as a precipitate. The precipitate was collected by filtration, washed with cold ethyl acetate and dried in vacuo to yield 0.887 g. (O-Bzl)Ser-Asn.HCl.

What is claimed is:

1. The process for the preparation of the peptide having the structure,

< Glu-Ala-Lys-Ser-Gln-Gly-Gly-Ser-Asn, which comprises converting the blocked heptapeptide hydrazide having the structure, <Glu-Ala-(ε-R)Lys-(O-R₁')Ser-Gln-Gly-Gly-NH-
NH₂ to the corresponding azide and condensing said azide with the hydroxy blocked or unblocked dipeptide, (O-R$_2$)Ser-Asn to obtain the blocked nonapeptide having the structure, < Glu-Ala-(ε-R)Lys-(O-R$_1$')Ser-Gln-Gly-Gly-(O-R$_2$)Ser-Asn wherein
R is the protecting group for the ε-amino of the lysyl moiety selected from the group consisting of formyl, toluene sulfonyl, benzyloxycarbonyl; 2,6-dichlorobenzyloxycarbonyl, p-nitrobenzyloxycarbonyl, 2-bromobenzyloxycarbonyl, 2-chlorobenzyloxycarbonyl; 2,2,2-trichloroethoxycarbonyl and isonicotinyloxycarbonyl,
R$_2$ is hydrogen or a protecting group for the hydroxy group of the seryl moiety, selected from the group consisting of benzoyl, t-butyl, benzyl,
R$_1$' is hydrogen or a protecting group for the hydroxy group of the seryl moiety selected from the group consisting of t-butyl and benzyl, and removing said protecting groups.

2. The process for the preparation of the peptide having the structure,

< Glu-Ala-Lys-Ser-Gln-Gly-Gly-Ser-Asn, which comprises condensing the blocked heptapeptide active ester having the structure, < Glu-Ala-(ε-R$_3$)Lys-(O-R$_4$')Ser-Gln-Gly-Gly-R$_6$ with the hydroxy blocked or unblocked dipeptide, (O-R$_5$)Ser-Asn wherein
R$_3$ is the protecting group for the ε-amino of the lysyl moiety selected from the group consisting of INOC, trifluoroacetyl, phthaloyl, tosyl, p-nitrobenzyloxycarbonyl, TROC and FMOC;
R$_4$' is hydrogen, p-nitrobenzyl or benzoyl,
R$_5$ is hydrogen or a protecting group for the hydroxy group of the seryl moiety, selected from the group consisting of benzyl, substituted benzyl wherein the substituent is o-chloro or p-nitro; t-butyl and benzoyl,
R$_6$ is an active ester selected from the group consisting of 1-hydroxybenzotriazole ester, N-hydroxysuccinimide ester and p-nitrophenyl ester, to obtain the blocked nonapeptide having the structure, < Glu-Ala-(ε-R$_3$)Lys-(O-R$_4$')Ser-Gln-Gly-Gly-(O-R$_5$)Ser-Asn, and removing said blocking groups.

3. The process according to claim 1 for the preparation of the peptide having the structure, < Glu-Ala-Lys-Ser-Gln-Gly-Gly-Ser-Asn, which comprises converting the blocked heptapeptide hydrazide having the structure, < Glu-Ala-(ε-INOC)Lys-(O-Bzl)Ser-Gln-Gly-Gly-NH-NH$_2$ to the corresponding azide by the action of isoamyl nitrite and condensing said azide with the blocked dipeptide, (O-Bzl)Ser-Asn.HCl to obtain the blocked nonapeptide having the structure, < Glu-Ala-(ε-INOC)Lys-(O-Bzl)Ser-Gln-Gly-Gly-(O-Bzl)Ser-Asn and removing the benzyl group with hydrogen fluoride and anisole and removing the INOC group with hydrogen and Pd/C catalyst.

4. The compounds having the structure,

< Glu-Ala-(ε-R$_8$)Lys-(O-R$_9$)Ser-Gln-Gly-Gly-(O-R$_{10}$)Ser-Asn wherein
R$_8$ is the protecting group for the ε-amino of the lysyl moiety selected from the group consisting of formyl, toluene sulfonyl, benzyloxycarbonyl; 2,6-dichlorobenzyloxycarbonyl, p-nitrobenzyloxycarbonyl, 2-bromobenzyloxycarbonyl, 2-chlorobenzyloxycarbonyl; 2,2,2-trichloroethoxycarbonyl, isonicotinyloxycarbonyl, trifluoroacetyl, phthaloyl, TROC and FMOC,
R$_9$ and R$_{10}$ are independently hydrogen or
R$_9$ and R$_{10}$ are protecting groups for the hydroxy group of the seryl moieties, independently selected from the group consisting of benzoyl, t-butyl, benzyl and substituted benzyl wherein the substituent is o-chloro or p-nitro.

5. The compounds having the structure,

< Glu-Ala-(ε-R$_8$)Lys-(O-R$_9$)Ser-Gln-Gly-Gly-R$_7$ wherein
R$_8$ is the protecting group for the ε-amino of the lysyl moiety selected from the group consisting of formyl, toluene sulfonyl, benzyloxycarbonyl; 2,6-dichlorobenzyloxycarbonyl, p-nitrobenzyloxycarbonyl, 2-bromobenzyloxycarbonyl, 2-chlorobenzyloxycarbonyl; 2,2,2-trichloroethoxycarbonyl, isonicotinyloxycarbonyl, trifluoroacetyl, phthaloyl, TROC and FMOC,
R$_9$ is hydrogen or the protecting group for the hydroxy group of the seryl moiety, selected from the group consisting of benzoyl, t-butyl, benzyl and substituted benzyl wherein the substituent is o-chloro or p-nitro,
R$_7$ is —NH—NH$_2$, OH, 1-oxybenzotriazole, N-oxysuccinimide, p-nitrophenoxy or OCH$_3$.

6. The compounds having the structure,

< Glu(or BOC-Gln)-Ala-(ε-R$_8$)Lys-(O-R$_9$)Ser-Gln-Gly-Gly-O-CH$_2$-φ-resin wherein $R_8$ is the protecting group for the ε-amino of the lysyl moiety selected from the group consisting of formyl, toluene sulfonyl, benzyloxycarbonyl; 2,6-dichlorobenzyloxycarbonyl, p-nitrobenzyloxycarbonyl, 2-bromobenzyloxycarbonyl, 2-chlorobenzyloxycarbonyl; 2,2,2-trichloroethoxycarbonyl, isonicotinyloxycarbonyl, trifluoroacetyl, phthaloyl, TROC and FMOC, $R_9$ is hydrogen or the protecting group for the hydroxy group of the seryl moiety, selected from the group consisting of benzoyl, t-butyl, benzyl and substituted benzyl wherein the substituent is o-chloro or p-nitro.

7. The compounds having the structure,

< Glu-Ala-(ε-$R_8$)Lys-(O-$R_9$)Ser-Gln-Gly-$R_7$ wherein $R_8$ is the protecting group for the ε-amino of the lysyl moiety selected from the group consisting of formyl, toluene sulfonyl, benzyloxycarbonyl; 2,6-dichlorobenzyloxycarbonyl, p-nitrobenzyloxycarbonyl, 2-bromobenzyloxycarbonyl, 2-chlorobenzyloxycarbonyl; 2,2,2-trichloroethoxycarbonyl, isonicotinyloxycarbonyl, trifluoroacetyl, phthaloyl, TROC and FMOC, $R_9$ is hydrogen or the protecting group for the hydroxy group of the seryl moiety, selected from the group consisting of benzoyl, t-butyl, benzyl and substituted benzyl wherein the substituent is o-chloro or p-nitro, $R_7$ is —NH—$NH_2$, OH, 1-oxybenzotriazole, N-oxysuccinimide, p-nitrophenoxy or $OCH_3$.

8. The compounds having the structure,

< Glu(or BOC-Gln)-Ala-(ε-$R_8$)Lys-(O-$R_9$)Ser-Gln-Gly-O-$CH_2$-φ-resin wherein $R_8$ is the protecting group for the ε-amino of the lysyl moiety selected from the group consisting of formyl, toluene sulfonyl, benzyloxycarbonyl; 2,6-dichlorobenzyloxycarbonyl, p-nitrobenzyloxycarbonyl, 2-bromobenzyloxycarbonyl, 2-chlorobenzyloxycarbonyl; 2,2,2-trichloroethoxycarbonyl, isonicotinyloxycarbonyl, trifluoroacetyl, phthaloyl, TROC and FMOC, $R_9$ is hydrogen or the protecting group for the hydroxy group of the seryl moiety, selected from the group consisting of benzoyl, t-butyl, benzyl and substituted benzyl wherein the substituent is o-chloro or p-nitro.

* * * * *